United States Patent
Widra

(10) Patent No.: US 6,746,836 B1
(45) Date of Patent: Jun. 8, 2004

(54) ALPHA-KERATOSE AS A BLOOD PLASMA EXPANDER AND USE THEREOF

(76) Inventor: Abe Widra, 3321 Glenwood Cir., Holiday, FL (US) 34691

( * ) Notice: Subject to any disclaimer, the term of this patent is extended or adjusted under 35 U.S.C. 154(b) by 318 days.

(21) Appl. No.: 09/840,197

(22) Filed: Apr. 23, 2001

Related U.S. Application Data

(60) Provisional application No. 60/254,249, filed on Dec. 8, 2000.

(51) Int. Cl.$^7$ .............................. A01N 1/00; A61K 35/24
(52) U.S. Cl. ........................... 435/1.1; 435/1.2; 424/543
(58) Field of Search ........................... 435/1.1, 1.2, 1.3, 435/29; 424/543; 514/23

(56) References Cited

U.S. PATENT DOCUMENTS

| | | | | |
|---|---|---|---|---|
| 3,970,614 A | * | 7/1976 | Goodwin | 260/123.7 |
| 4,001,401 A | * | 1/1977 | Bonsen et al. | 424/177 |
| 4,167,622 A | * | 9/1979 | Holzer | 536/111 |
| 4,370,472 A | * | 1/1983 | Igarashi et al. | 536/1.1 |
| 4,570,629 A | * | 2/1986 | Widra | 604/304 R |
| 4,629,698 A | * | 12/1986 | Nitsch et al. | 435/65 |
| 5,039,520 A | * | 8/1991 | Hunter | 424/83 |
| 5,218,108 A | * | 6/1993 | Sommermeyer et al. | 536/111 |
| 5,276,138 A | | 1/1994 | Yamada et al. | 530/357 |
| 5,405,742 A | | 4/1995 | Taylor | 435/1 |
| 5,470,841 A | * | 11/1995 | Forster et al. | 514/60 |
| 5,514,536 A | | 5/1996 | Taylor | 435/1.2 |
| 5,571,801 A | | 11/1996 | Segall et al. | 514/59 |
| 5,652,274 A | | 7/1997 | Martin | 514/724 |
| 5,698,536 A | | 12/1997 | Segall et al. | |
| 5,905,141 A | | 5/1999 | Rausch et al. | 530/385 |
| 5,945,272 A | | 8/1999 | Segall et al. | 435/1.2 |
| 6,066,316 A | | 5/2000 | Shiojima et al. | 424/70.19 |
| 6,110,504 A | | 8/2000 | Segall et al. | 424/663 |

FOREIGN PATENT DOCUMENTS

| | | | | |
|---|---|---|---|---|
| EP | 0089152 | | 9/1983 | A31L/15/04 |
| JP | 08-332087 | * | 12/1996 | |
| JP | 10077210 | | 3/1998 | A61K/7/00 |

OTHER PUBLICATIONS

Artz, C.P., 1973. Severe burns: current concepts of specialized care, Modern Medicien, Apr. 30, pp. 40–47.*

Birke, G., Liljedahl. S.O., Backdahl. M. and Nylen B. 1964. Studies on burns.*

VIII. Analysis of mortality and length of hospital care for 603 burned patients referred for primary treatment. Acta chir. Scand. Supp. 337:1–21.*

Burke, J.F. 1967. Fluid therapy using colloid. (Symp.,6th Nat'l Burn Seminar) J. Trauma 7:73–74.

Cochrane Injuries Group Albumin Reviwers. 1998. Human albumin administration in critically ill patients: systematic review of randomized controlled trials. Brit. Med. J. 317: 235–240.

Crewther. W.G.. Fraser. R.B.D., Lennox, F.G., and Lindley. H., 1965. Chemistry of keratins.pp. 191–346 in Advances in Protein Chemistry. vol. 20, Academic Press. N.Y.

Fox. C.L., 1967. Treatment of burns. Modern Treatment 4:1195–1313.

HE X.M. and Carter. D.C. 1992. Atomic structure and chemistry of human serum albumin. Nature 358:209–215.

Hosek, R. 1994. Colloids versus crystalloids which therapay is right! Univ. of Iowa (Ames) P & T News: vol. 14. #10. pp. 1–9.

O'Donnell., I. J. & Thompson, E.O.P., 1961. Studies on oxidized wool IV. Fractionation of proteins extracted from wool on DEAE–cellulose using buffers containing 8M urea. Aust. J. of Biol. Sci. 14:461–474

Peters. Jr. T., 1970 Serum albumin. Adv. Clin. Chem. 13: 37–111.

Pruitt. B.A.. 1978. Fluid and electrolyte replacement in the burned patient. Surgical Clinics of North America (Symp on Burns) 58:1291–1301.

Pumper. R.W., Yamashiroya, H.M., and Molander, L.T.. 1965. Growth of mammalian cells in a heat stable, dialyzable medium. Nature 207:662–663.

Rhodes, H.J., Potter, B., and Widra. A.. 1967. Characteristics of the alpha–keratose fraction of human hair inducing ascosporogenesis in Nannizzia grubyia. Mycopathlogia 33:345–348.

Ricketts. C.R.. 1966. Proteins and colloid solutions used in burns treatment, pp. 48–60 in Research in Burns. 2nd Intl. Congress, Wallace. A.B. & Wilkinson. A.W., Eds., Livingstone Ltd., London.

Roe, C.F., 1966, Evaporative water loss in third degree burns. pp. 178–183 in Research in Burns, 2nd Intl. Congress, Wallace, A.B. & Wilkinson, A.W. Eds., Livingstone, Ltd. London.

Roe, C.F. 1967. Evaporative heat loss (Symp.. 6th Natl.. Burn Seminar) J. Trauma 7:147–152.

Sobinsky, K.R. and Flanigan, D.P., 1986 Antibiotic binding to polytetraflourpoethylene via glucosomineglycan–keratin luminan coating. Surgery 106v4:(629–634).

Taylor, W.G., Taylor, M.J., Lewis, N.J., and Pumper, R.W., 1972 A serum substitute for mammalian cells in culture. I. Biological efficacy of whole and fractionated peptone dialysate. Proc. Soc.Exp.Biol.Med. 139:(96–99).

(List continued on next page.)

Primary Examiner—Sandra Saucier
(74) Attorney, Agent, or Firm—Holland & Knight LLP

(57) ABSTRACT

A plasma expander and blood substitute comprising a therapeutic amount if a solution of alpha-keratose, a soluble fraction of keratin, as an oncotic agent with nutrient growth properties suitable as a transport vehicle for the natural or synthetically formed elements of blood. The solution of alpha-keratose is non-antigenic, does not require blood typing, is free of disease producing viruses and may be stored indefinitely at ambient temperatures in the lyophilized state.

3 Claims, No Drawings

OTHER PUBLICATIONS

Widra, A., 1966. Ascosporogenesis by Nannizzia grubyia on a soluble fraction of keratin. Mycopathologia 30:141–144.

Widra, A., 1989 Skin, synthtic. pp. 335–345 in Encyclopedia of Polymer Science and Engineering, 2nd Edition. John Wiley & Sons, N.Y.

Ewald, R.A. Effects of Intravenous Infusion of Feather Keratin: Preliminary Characterization and Evaluation as a Plasma Expander. Proceedings for the Society for Experimental Biology and Medicine. Jan. 1964, vol. 115. No. 1, pp. 130–133.

O'Donnell. , I. J. & Thompson, E.O.P., 1961. Studies on oxidized wool IV. Fractionation of proteins extracted from wool on DEAE–cellulose using buffers containing 8M urea. Aust. J. of Biol. Sci. 14:461–474.

Peters. Jr. T., 1970 Serum albumin. Adv. Clin. Chem. 13: 37–111.

Pruitt. B.A.. 1978 Fluid and electrolyte replacement in the burned patient. Surgical Clinics of North America (Symp on Burns) 58:1291–1301.

Pumper. R.W. Yamashiroya. H.M.. and Molander, L.T.. 1965. Growth of mammalian cells in a heat stable, dialyzable medium. Nature 207: 662–663.

Rhodes, H.J., Potter, B., and Widra. A.. 1967. Characteristics of the alpha–keratose fraction of human hair inducing ascosporogenesis in Nannizzia grubyia. Mycopathologia 33:345–348.

Ricketts. C.R. 1966. Proteins and Colloid solutions used in burns treatment. pp. 48–60 in Research in Burns. 2 nd Intl. Congress. Wallace. A.B. & Wilkinson. A.W. Eds., Livingstone Ltd., London.

Roe, C.F.. 1966. Evaporative water loss in third degree burns. pp. 178–183 in Research in Burns. 2nd Intl. Congress. Wallace. A.B. & Wilkinson. A.W.. Eds., Livningstone. Ltd. London.

Roe, C.F. 1967. Evaporative heat loss. (Symp.. 6th Natl.. Burn Seminar) J. Trauma 7: 147–152.

Sobinsky, K.R. and Flanigan, D.P., 1986 Antiboitic binding to polytetraflouroethylene via glucosmineglycan–keratin luminan coating. Surgery 100v4:(629–34).

* cited by examiner

ALPHA-KERATOSE AS A BLOOD PLASMA EXPANDER AND USE THEREOF

CROSS REFERENCE TO RELATED APPLICATIONS

This application is a utility application based upon and claiming priority of provisional application No. 60/254,249, filed Dec. 8, 2000, the disclosure of which is incorporated by reference herein.

BACKGROUND OF THE INVENTION

1. Field of the Invention

This invention relates to a novel use for a protein derived from keratin. In particular, it proposes the use of alpha-keratose as a blood plasma expander, for the preservation and transportation of organs and for the formed elements of blood.

2. Description of the Background Art

Heretofore, an intense research effort has been made and many materials have been developed that lend themselves for possible use as a blood plasma expander. A blood plasma expander is generally used for fluid replacement in the treatment of extensively burned individuals to remove burn toxins and/or prevent burn shock. Fluid replacement therapy may also be required by individuals with open wounds and extensive external and/or internal bleeding, immunologic defects, clotting problems, or severe diarrhea.

Blood plasma expanders have been made from materials consisting of crystalloid solutions or colloidal-like polymeric solutions. The crystalloid materials include saline, compositions of saline and glucose, Hartmann's solution, and Ringer's solution. The colloidal-like polymeric materials include pectin, gelatin, albumin, hydroxyethyl starch, polyvinyl pyrrolidone, dextran and cellulose derivatives.

Some blood plasma expanders have been made from blood and blood fractions. However, the use of blood and blood fractions is fraught with disadvantages. For example, the use of whole blood often is accompanied with the risk of transmission of hepatitis-producing viruses or other viruses which complicate the patient's recovery. Additionally, the use of whole blood requires blood-typing and cross-matching to avoid immunohematological problems and interdonor incompatibility.

Therefore, a blood fraction plasma, which is a physiologically balanced colloidal solution that fulfills many of the requirements of a blood volume expander, cannot be safely used for this purpose unless further efforts in time and expense are made to remove infectious agents. It would also be advantageous to remove isoagglutinins. Clearly it is desirable to use non-blood based blood substitutes. In view of the above presentation, it becomes immediately apparent that a need exists for a therapeutic product useful as a blood plasma expander without the above drawbacks.

Plasma and albumin, as blood plasma expanders, have disadvantages in their availability, initial expense, storage, and risk of viral infection. Whereas, dextrans of high molecular weight are especially useful in that they are not excreted as rapidly as low molecular weight dextrans, they present the dangers of rouleaux formation, sludging of erythrocytes, and possible anaphylaxis. Hence the compromise using dual high and low molecular weights of oncotic agents with differential clearance rates, such as dextrans and hydroxyethyl starches (HES) to overcome this problem (U.S. Pat. No. 5,945,272).

Since experimental work with mice has shown the use of serum to be no more effective than its sodium content (Rosenthal; cited by Fox, 1967) and the use of colloids serves both to raise venous pressure and to reduce sodium excretion, it should be possible to devise a salt-colloid mixture suitable for fluid replacement therapy.

It would therefore be advantageous if the colloid portion of a blood plasma expander could be a non-antigenic aqueous drug and virus-free solution which could act as an oncotic agent, which could serve as food for various tissue cells, which could be used for cryopreservation of tissues preparatory to transplantation, which could be freely miscible with other electrolytes, nutrients, oncotics, and oxygen bearing substances known in the blood transfusion art and which could be sterilized and stored long term for use at ambient room temperatures.

Accordingly, there is a critical and continual need for a blood plasma expander that can be used for volume deficiency shock, as an alleviant in anaphylactic and allergic shock, for replacing plasma lost after burns and as a result of diarrhea and for preserving and transporting organs.

OBJECTS OF THE INVENTION

Accordingly, it becomes an object of the invention to provide a salt-colloid mixture suitable as a blood plasma expander for all blood types, which does not have the drawbacks of plasma/albumin (problems with donor accessibility, possible viral infection, foreign antigens, cold storage), or the balancing of high and low molecular weight solutions of dextrans or hydroxyethyl starches.

Another object of the invention is to provide a novel agent useful as a blood and plasma expander by dint of molecular size large enough to allow it to maintain intravascular residence and osmotic pressure for a prolonged time.

Yet another object of the invention is to provide a blood and plasma expander which can serve as a source of nutrient growth factors for the cells it bathes.

A further object of the invention is to provide a useful blood and plasma expander which is miscible and compatible with all components of blood and is itself non-toxic, non-antigenic, and non-pyrogenic.

Still a further object of the invention is to provide a blood substitute and plasma expander which is stable under prolonged storage and is either safely discharged from the body or degraded to nutrient components.

Another object of the invention is to provide a blood-free plasma expander and blood substitute for use in a subject in need thereof, comprising a solution of alpha-keratose.

Yet another object of the invention is to provide a pharmaceutical composition useful as a blood plasma expander and blood substitute comprising a therapeutically effective amount of alpha-keratose that is soluble in aqueous and physiological fluids.

Another object of the invention is to provide a pharmaceutically acceptable carrier comprising a solution of alpha-keratose.

Yet another object of the invention is to provide a buffer comprising a solution of alpha-keratose.

Still another object of the invention is to provide a method of treating a human in need of blood by intravenously administering to the human an effective amount of a blood substitute comprising alpha-keratose.

Still yet another object of the invention is to provide a method for increasing the volume of the blood circulatory system wherein the method comprises transfusing into a system having a decreased volume, a quantity of a blood volume expander which consists of a solution of alpha-keratose, wherein the quantity is transfused in an effective amount to increase said volume.

Another object of the invention is to provide a method for the treatment of shock which comprises administering into the circulatory system of a mammal in shock, a blood plasma expander consisting of a solution of alpha-keratose, in an effective amount to alleviate said shock.

Yet another object of the invention is to provide a method for maintaining an isolated mammalian organ in a viable state which method comprises perfusing the organ with an effective amount of a perfusate consisting of a solution of alpha-keratose.

Another object of the invention is to provide an oncotic agent which has been shown to be a complete substitute for fetal calf serum in tissue cultured cells which have been adapted to growth in peptone dialysate.

Still another object of the invention is to provide a method for removing pathogens, poisons or toxins from blood present in a patient, the method comprising the steps of infusing the patient with a sufficient volume of a blood substitute solution comprising at least one water soluble oncotic agent while removing an equal volume of blood from the patient to reduce the hematocrit of the patient to 10 to 15%; separating the blood cells of the blood from the pathogens, toxins or poisons; resuspending the blood cells in a blood plasma expander comprising a water soluble oncotic agent to produce a blood cell comprising solution; and infusing the patient with the blood cell comprising solution; whereby the pathogens, toxins or poisons are removed from the blood of the patient.

The foregoing has outlined some of the pertinent objects of the present invention. These objects should be construed to be merely illustrative of some more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims.

SUMMARY OF THE INVENTION

This invention is concerned with the use of soluble keratins as a blood plasma expander. In addition, the soluble keratins can be used as a vehicle for transportation and preservation of organs and the formed elements of blood.

A feature of the present invention is to provide a novel agent useful as a blood and plasma expander by dint of molecular size large enough to allow it to maintain intravascular residence and osmotic pressure for a prolonged time.

Yet another feature of the present invention is to provide a blood and plasma expander which can serve as a source of nutrient growth factors for the cells it bathes.

A further feature of the present invention is to provide a useful blood and plasma expander which is miscible and compatible with all components of blood and is itself non-toxic, non-antigenic, and non-pyrogenic.

Still a further feature of the present invention is to provide a blood substitute and plasma expander which is stable under prolonged storage and is either safely discharged from the body or degraded to nutrient components.

Another feature of the present invention is to provide a blood-free plasma expander and blood substitute for use in a subject in need thereof, comprising a solution of alpha-keratose.

Yet another feature of the present invention is to provide a pharmaceutical composition useful as a blood plasma expander and blood substitute comprising a therapeutically effective amount of alpha-keratose that is soluble in aqueous and physiological fluids.

Another feature of the present invention is to provide a pharmaceutically acceptable carrier comprising a solution of alpha-keratose.

Yet another feature of the present invention is to provide a buffer comprising a solution of alpha-keratose.

Still another feature of the present invention is to provide a method of treating a human in need of blood by intravenously administering to the human an effective amount of a blood substitute comprising alpha-keratose.

Still yet another feature of the present invention is to provide a method for increasing the volume of the blood circulatory system wherein the method comprises transfusing into a system having a decreased volume, a quantity of a blood volume expander which consists of a solution of alpha-keratose, wherein the quantity is transfused in an effective amount to increase said volume.

Another feature of the present invention is to provide a method for the treatment of shock which comprises administering into the circulatory system of a mammal in shock, a blood plasma expander consisting of a solution of alpha-keratose, in an effective amount to alleviate said shock.

Yet another feature of the present invention is to provide a method for maintaining an isolated mammalian organ in a viable state which method comprises perfusing the organ with an effective amount of a perfusate consisting of a solution of alpha-keratose.

Another feature of the present invention is to provide an oncotic agent which has been shown to be a complete substitute for fetal calf serum in tissue cultured cells which have been adapted to growth in peptone dialysate.

Still another feature of the present invention is to provide a method for removing pathogens, poisons or toxins from blood present in a patient, the method comprising the steps of infusing the patient with a sufficient volume of a blood substitute solution comprising at least one water soluble oncotic agent while removing an equal volume of blood from the patient to reduce the hematocrit of the patient to 10 to 15%; separating the blood cells of the blood from the pathogens, toxins or poisons; resuspending the blood cells in a blood plasma expander comprising a water soluble oncotic agent to produce a blood cell comprising solution; and infusing the patient with the blood cell comprising solution; whereby the pathogens, toxins or poisons are removed from the blood of the patient.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

DETAILED DESCRIPTION OF THE INVENTION

Keratins are unique to the animal kingdom. Keratins are complex proteins found throughout the tissues of the body most notably in skin, hair, nail, claw, horn, hoof, fur, wool, quill, and feather.

The colloid portion, or part of the colloid portion of the solution of the present invention, is a non-antigenic, nutrient, soluble fraction of keratin.

Keratin derivatives are chemically and immunologically distinct according to the species from which derived, and according to the method of extraction and/or solubilization. For example, keratin derivatives can be extracted and/or solubilized by reduction by thiol groups and solution in alkali, oxidation, sulfitolysis and solution in urea, oxidative sulfitolysis or enzymatic cleavage (Crewther et al., 1965). Such soluble keratin derivatives may be sized by column chromatography, degraded to smaller fragments, recombined in novel ways, or otherwise manipulated, filter sterilized, and stored at room temperature, obviating both cold storage and viral threat.

The present invention embodies the soluble alpha-keratose fraction of insoluble alpha-keratin; i.e., the fibrous protein microfibrils in the form of intertwined filamentous alpha-helices found in native keratins. The preferred source of material is human hair (abundant, inexpensive, renewable, and non-antigenic) in which the hair cortex is packed with alpha-keratin.

The preparation of alpha-keratose from human hair (Widra, 1966) or wool "tops"(Widra 1989) was developed as an integral and essential component of a series of biodegradable hydrophilic wound covers, as described by Widra (1986). The laboratory preparation method is repeated here, wherein the first five steps may be conveniently performed in a single one liter Erlenmeyer flask:

1. Twelve grams of human hair is degreased with ether-alcohol (1:1) and then washed in water.
2. 320 ml of water and 80 ml of concentrated (40%) peracetic acid is added to the hair.
3. The hair-acid mixture is refrigerated at 4° C. with constant stirring for 24 hours.
4. The hair is then freed of the peracetic acid by decantation and thorough washing with separate water rinses.
5. The washed hair is then covered with 800 ml of 3N ammonium hydroxide, refrigerated, and stirred for 24 hours at a temperature of 4° C.
6. The total soluble protein (TP) fraction is then cleared of solids by centrifugation and coarse filtration to remove any visible particulates.
7. The TP fraction is dialyzed through cellulose tubing (14,000 molecular weight cut off) against water.
8. Alpha-keratose is precipitated from the dialyzed TP fraction with small incremental additions of 0.1 N hydrochloric acid, stirring between additions. This procedure is continued until no further precipitate forms.
9. The white precipitate is collected by centrifugation and the supernatant gamma-keratose is discarded.
10. The alpha-keratose precipitate is washed in water, recentrifuged, then resolubilized in 0.1 N ammonium hydroxide.
11. A second cycle of precipitation, washing, and solubilization is run on the alpha-keratose before final dialysis against water, microfiltration (22 micra), and storage in a sterile container. (The alpha-keratose solution may be concentrated by simple pervaporation through the dialysis bag, then assayed for protein content.)

The resulting light amber solution of alpha-keratose is faintly positive to Nessler's solution and just on the alkaline side of neutrality (pH 7.1–7.2).

The average molecular weight of the alpha-keratose fraction of human hair determined by ultracentrifugation is 45,000 daltons (Widra, 1989).

Alpha-keratose from human hair (15 ml, 5 mg per ml) failed to raise antibodies in a rabbit, whereas gamma keratose did so, cross reacting with both TP and alpha-keratose (Widra, 1966). The procedures freeing and fragmenting the linear alpha-keratin fibrils from matrix (gamma keratose) proteins may also destroy antigenicity. Alpha-keratose, itself, may be resolved into 3 subfractions by disc electrophoresis on acrylamide gel (Rhodes et al, 1967). The main subfraction is characteristic of serum albumin in its speedy migration to the anode, isoelectric point (pH 4.8), high sulfur content, and paucity of tryptophane residues (Peters, 1970; O'Donnell & Thompson, 1961; He & Carter, 1992).

The total soluble protein (TP) or the alpha-keratose derived from human hair is non-toxic to cells in tissue culture using primary human embryonic kidney cells, a Wistar Institute (Philadelphia, Pa.) strain of diploid human embryonic lung cells (WI38), African green monkey kidney cells, and heteroploid rabbit heart cells. Furthermore, in such cells adapted to growth in Bacto-peptone supplement as a substitute for fetal bovine serum. (FBS) (Pumper et al 1965; Taylor et al 1972), alpha-keratose could completely replace the peptone and/or FBS as a nutrient growth factor (Widra & Pumper 1981).

Since alpha-keratose is miscible in all proportions with the usual physiologic salt/electrolyte crystalloid solutions used in transfusion therapy, this novel oncotic and nutrient agent may be used to form a salt-colloid mixture suitable for fluid replacement therapy.

The blood plasma expander of this invention is an aqueous solution without any of the cells normally found in whole blood or blood plasma and, as such, can generally be safely stored for much longer periods than whole blood or blood plasma and can be used without cross-matching or haplotyping between donor and recipient. Since the blood plasma expander solutions of this invention are totally synthetically produced there is substantially no risk of blood contaminants, such as bacterial, viral or other blood contaminants being introduced into the solutions. This is especially important in this age of hepatitis, AIDS and other blood transmitted diseases.

In greater detail, the present invention comprises a mixture of components which when placed in aqueous solution may be used to expand the blood plasma volume of a subject in need thereof. The forgoing components may be provided as a dry sterile mixture to which sterile diluent such as water, saline solution or dextrose solution may be added to form an aqueous solution. If provided as a dry sterile mixture, the materials may be provided in a sterile container suitable for mixture with sterile diluent such as sterile water, sterile saline, sterile dextrose solution, or a suitable commercially available electrolyte solution. Alternatively the mixture of materials may be provided in a sterile container as an aqueous solution.

In the following examples, production was scaled up and powdered alpha-keratose was manufactured as follows:

1. 76.7 g of human hair were swirled in ethyl ether and then washed with distilled water (dH2O).
2. 1000 ml of dH2O and 250 ml peracetic acid were added.
3. Solution was refrigerated at 4° C. overnight with occasional swirling.
4. The solution was decanted to remove the peracetic acid and the solids washed with 3 liters of dH2O on a Buchner funnel.

5. The washed solids (hair) were immersed in 2.5 liters of 3N ammonium hydroxide and stirred at 4° C. overnight.
6. The solids were removed by centrifugation at 5000×G for 15 minutes.
7. The supernate was then clarified through Whatman 54 paper by vacuum.
8. The solution was dialyzed overnight against flowing dH2O.
9. Material was precipitated by incremental addition of 0.1N HCl until no more precipitate was observed to form.
10. The precipitate was collected by vacuum filtration on Whatman 54 paper and washed with dH2O.
11. The precipitate was resolubilized in 0.3N ammonium hydroxide.
12. Solution was dialyzed against flowing dH2O overnight.
13. Solution was removed from dialysis and filtered through Millipack 200 (0.22 micra) into a depyrogenated tray for lyophilization.
14. Material was lyophilized and collected in a class 10,000 area, transferred to a biological safety cabinet (class 100), then stored in sterile containers.

This totally soluble, sterile, dry material gives "off-the-shelf" convenience and flexibility in preparing solutions with different concentrations of alpha-keratose.

The following example is put forth so as to provide those of ordinary skill in the art with a complete disclosure and description of how to carry out the synthesis of the invention and is not intended to limit the scope of what the inventor regards as his invention. Efforts have been made to ensure accuracy with respect to numbers used (e.g., amounts, temperature, etc.), but some experimental error and deviation should be accounted for.

EXPERIMENTAL EXAMPLE

In order to ascertain the usefulness of alpha-keratose as a plasma expander (as well as extended uses to encompass hypothermic organ perfusion or mixtures with oxygen carriers such as manufactured hemoglobins or perfluorocarbons) a 32 lb (14.5 kg) female beagle dog was recruited for a rigorous test under closely monitored conditions by a team of veterinarians directed by Dr. David H. Knight at the University of Pennsylvania School of Veterinary Medicine, Philadelphia, Pa. The test on the appropriately anesthetized animal involved a precipitous loss of at least 25% of blood volume (300 ml) within 5 minutes, similar to acute hemorrhage, a 23 minute wait, then rapid replacement with 300 ml of alpha-keratose (2.5% {w/v} in Normosol-R pH 7.4) within 5.5 minutes. Normosol-R pH 7.4 and similar preparations are commercially available osmotic and pH balanced electrolyte solutions. Physical and chemical parameters were measured at regular intervals:

1. a pre-bleed baseline on the fasting anesthetized animal;
2. at the 30 minute post-bleed point;
3. at the 30 minute post infusion point;
4. the one hour post-infusion point;
5. the 3 hour post infusion point;
6. the 6 hour post infusion point; and
7. following resuscitation, the 24 hour post infusion point.

Total duration of anesthesia was 8 hours, 50 minutes during which time a Normosol R pH 7.4 drip was maintained at 3.5 ml/kg/hr for the test period.

At the end of the experiment, 300 ml of Normosol R pH 7.4 was given rapidly to bring the total volume to one liter for the day.

Effect on Physical Parameters

The data shows an expected drop in blood pressure and rise in heart rate after bleeding, and a transitory rise in temperature following colloid infusion, with a return to normal in 6 hours as shown in TABLE 1. Calculated serum osmolarity was normal throughout the experiment

TABLE 1

|  | Anesthetized Baseline | 30 minutes post bleed | 30 minutes post infusion | 1 hour post infusion | 3 hours post infusion | 6 hours post infusion | 24 hours post infusion |
|---|---|---|---|---|---|---|---|
| Blood pressure: Mean bp (direct arterial) | 64 | 28 | 51 | 54 | 88 | 77 | N/A |
| Systolic/Diastolic | 111/50 | 40/24 | 76/43 | 82/42 | 121/76 | 137/58 | N/A |
| Heart rate (beats/min) via electocardiogram | 73 | 153 | 132 | 132 | 149 | 139 | N/A |
| Temperature 99.7 F. on arrival | 96.2 | 95.1 | 101.5 | 101.5 | 101.5 | 99.7 | N/A |
| Calculated Serum Osmolarity Mosmol/kg Normal range 250–350 | 276 | 277 | 288 | 283 | 281 | 278* | 290 |

*After taking these readings, physical monitors were removed and dog was resuscitated.

This dog began with low levels of albumin and total protein both of which declined, possibly because of hemodilution, as fluid was absorbed into the blood pool. The albumin/globulin ratio, however remained normal at all times as shown in TABLE 2.

TABLE 2

|  | Anesthetized Baseline | 30 minutes post bleed | 30 minutes post infusion | 1 hour post infusion | 3 hours post infusion | 6 hours post infusion | 24 hours post infusion | Normal Range |
|---|---|---|---|---|---|---|---|---|
| SERUM TOTAL PROTEIN g/dL | 5.2 | 4.8 | 3.7 | 3.7 | 1.8 | 4.1 | 4.4 | 5.4–7.1 |
| ALBUMIN g/dL | 2.4 | 2.2 | 1.7 | 1.7 | 1.7 | 1.8 | 1.9 | 2.5–3.7 |
| GLOBULIN g/dL | 2.8 | 2.6 | 2.0 | 2.0 | 2.0 | 2.2 | 2.4 | — |
| A/G RATIO | .8 | .8 | .9 | .8 | .9 | .8 | .8 | — |

Effect on Formed Elements of Blood

Red and white cell counts were normal throughout the test period and recovery. The elevated hematocrit may be attributed to splenic contraction and release of red blood cells post-bleed. Platelets were reduced by loss of blood and subsequent colloid infusion, but recovered to an adequate level one hour post infusion, then to normal at the 3 hour mark as shown in TABLE 3.

The animal had one loose, bloody bowel movement after resuscitation at 6 hours post infusion, but walked about, appeared well, and was eating before the 24 hour blood sample was taken.

Effect on Blood Chemistries

The liver and kidneys are paramount in detoxification and excretion of new products designed for parenteral use. The liver enzyme profile of 4 tests appears unremarkable

TABLE 3

|  | Anesthetized Baseline | 30 minutes post bleed | 30 minutes post infusion | 1 hour post infusion | 3 hours post infusion | 6 hours post infusion | 24 hours post infusion | Normal Range |
|---|---|---|---|---|---|---|---|---|
| RBC ERYTHROCYTES M/uL | 4.17 | 5.12 | 5.56 | 4.82 | 5.31 | 5.38 | 4.94 | 5.90–8.87 |
| HGB HEMOGLOBIN g/dL | 10.1 | 12.1 | 13.2 | 11.6 | 12.6 | 12.8 | 11.7 | 14.2–20.5 |
| HCT HEMATOCRIT % | 28.3 | 35.0 | 38.4 | 33.2 | 36.4 | 37.3 | 34.0 | 42.3–60.2 |
| PLATELETS K/uL | 258 | 294 | 64.2 | 111 | 179 | 161 | 101 | 177–398 |

Manual differential counts of white blood cells and examination of RBC morphology gave an essentially normal picture throughout the test period. There was no evidence of anaphylaxis or toxicity to the animal, red cell damage, or elevated counts of eosinophils, basophils, lymphocytes, or monocytes as shown in TABLE 4.

throughout the 6 hour test period, only the SGOT rising significantly in the recovered animal, reflecting perhaps, the incipient breakdown of the oncotic agent. The slow rise in creatinine, reflecting a modest decline in renal function, may be due to the period of hypotension and renal ischemia after the bleed, especially in view of the fact that Normosol R pH

TABLE 4

|  | Anesthetized Baseline | 30 minutes post bleed | 30 minutes post infusion | 1 hour post infusion | 3 hours post infusion | 6 hours post infusion | 24 hours post infusion | Normal Range |
|---|---|---|---|---|---|---|---|---|
| EOSINOPHILS % | 4 | 9 | 3 | 7 | 5 | 5 | 0 | 0.00–20.0 |
| BASOPHILS % | 0 | 0 | 0 | 0 | 0 | 0 | 0 | 0.00–2.0 |
| LYMPHOCYTES % | 27 | 28 | 33 | 43 | 30 | 7 | 8 | 10.0–45.0 |
| MONOCYTES % | 7 | 1 | 1 | 1 | 1 | 3 | 10 | 1.00–13.0 |

7.4 administration was maintained at 3.5 ml/k/hr which is about half the normal rate for replacing incipient fluid loss during anesthesia. The total duration of anesthesia was 8 hours and 50 minutes. TABLE 5 shows the data taken during anesthesia through the 6 hour post infusion point. In addition, subsequent to recovery, data was taken for the 24 hour post infusion point.

TABLE 5

|  | Anesthetized Baseline | 30 minutes post bleed | 30 minutes post infusion | 1 hour post infusion | 3 hours post infusion | 6 hours post infusion | 24 hours post infusion | Normal Range |
| --- | --- | --- | --- | --- | --- | --- | --- | --- |
| SGPT u/L | 13 | 11 | 18 | 16 | 13 | 16 | 45 | 16–91 |
| SGOT u/L | 22 | 18 | 16 | 25 | 31 | 49 | 244 | 23–65 |
| ALKP u/L | 50 | 48 | 42 | 37 | 38 | 50 | 150 | 24–174 |
| GGT u/L | 10 | 9 | 7 | 6 | 6 | 9 | 8 | 7–24 |
| CREATININE mg/dL | 0.7 | 0.8 | 0.8 | 0.9 | 1.2 | 1.7 | 2.0 | 0.7–1.8 |

Subsequent testing of the animal's blood count, WBC differential panel at 48 hours and 7 days post infusion times to normality as shown in TABLE 6.

TABLE 6

|  | 48 Hours Post Infusion | 7 Days Post Infusion |
| --- | --- | --- |
| Serum TP/AG ratio | 6.1/0.8 | 6.4/0.8 |
| RBC | 4.94 | 5.38 |
| HGB | 11.8 | 13.2 |
| HCT | 34.2 | 38.1 |
| PLATELETS | 82.1 | 428 |
| EOSINOPHILS (%) | 4 | 10 |
| BASOPHILS (%) | 0 | 0 |
| LYMPHOCYTES (%) | 15 | 12 |
| MONOCYTES (%) | 7 | 9 |
| SGPT (ALT) | 49 | 40 |
| SGOT (ASP) | 89 | 25 |
| ALK P | 143 | 106 |
| GGT | 10 | 10 |
| CREATININE | 1.7 | 1.3 |
| SERUM OSMOLARITY (CALCULATED) | 291 | 283 |

In summary, the test animal was severely stressed by a loss of over 300 ml of blood (including samples drawn under prolonged anesthesia). This was replaced with 300 ml of 2.5% colloid (w/v) in a crystalloid solvent during a 5.5 minute time span without serious complications, thereby demonstrating the usefulness of alpha-keratose as an oncotic agent for achieving the objects of the invention. At the conclusion of all testing, the dog was eating and looking quite strong, showing no ill effects from the experiment.

The above experiment indicates that the alpha-keratose solution of the present invention provides a useful transport medium for the formed cellular elements of blood and maintains normal vascular osmotic pressure due to its oncotic properties. A protein, the extraction/genesis of which took place at refrigerator temperature (4° C., to prevent possible heat denaturation) is not subject to freezing under the same condition. Indeed, 2.5% alpha-keratose in salt solution does not freeze or become noticeably more viscous from 12° C. down to 2° C., thereby allowing its use in hypothermic applications of the transfusion art, such as, but not limited to, open-heart surgery and organ transplantation.

In addition, in the normal physiologic temperature range, the ability of alpha-keratose to act as a nutrient growth factor in a variety of tissue type, across several species lines (Widra & Pumper, 1981), enhances its usefulness as a perfusion agent for the maintenance of organs for transplantation.

Alpha-keratose has also served as a solvent vehicle for pharmaceuticals such as carbenicillin, tetracycline, and heparin (Widra, 1986) and, like albumin, has the stabilizing advantage of its innate amphoteric buffering capacity. Alone, or in combination with other hydrophilic biodegradable biopolymeric copolyelectrolytes, alpha-keratose forms a film upon dehydration (an open wound site, for example) and acts as a shield to maintain the potency (Sobinsky & Flanigan, 1986) of contained solutes and the integrity of the formed elements.

When it is necessary to treat a subject who has lost a significant amount of blood, generally up to about 30% to 40% of blood volume with a plasma expander, the mixture of the present invention may be administered intravenously or intravascularly as a sterile aqueous solution.

When used as a blood plasma expander in a hypovolemic subject, the solution according to the invention will be administered in an amount up to about 30% of the average blood volume of an average subject. If the subject is the size of an average adult male human being the average blood volume is about 5000 ml and the volume of the solution according to the invention will be up to about 1500 ml.

When used as a blood replacement in a severely hypovolemic subject or when used in a procedure in which the subject blood is deliberately removed, the solution will be administered as a sterile solution in an amount exceeding 30% of the average blood volume and will generally exceed 1500 ml.

When used as a plasma extender, which in general is in situations where 30% or less of the subject's normal blood volume is being added (usually after blood loss due to trauma or surgery), the solution according to the invention will usually be administered to a subject at normal body temperature for that mammalian subject.

The preservation or maintenance solution according to the invention is capable of protecting living tissues, such as skin, corneas, organs, such as, for example, heart, lung, kidney, liver or pancreas, and organ parts, such as, for example, muscles, pancreatic islets, heart valves, and the like. Such protection includes protection from damage caused by ischemia and/or anoxia during storage prior to transplantation in a subject.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

I claim:

1. A blood-free plasma expander and blood substitute for use in a subject in need thereof, consisting essentially of alpha-keratose dissolved in an electrolyte solution.

2. The blood free plasma expander and blood substitute according to claim 1 wherein the electrolyte solution is selected from the group consisting of sterile saline, mixed salts solution, and mixtures thereof.

3. A pharmaceutical composition useful as a blood plasma expander and blood substitute consisting essentially of a therapeutically effective amount of alpha-keratose dissolved in an electrolyte solution.

* * * * *